US011028431B2

United States Patent
Claes et al.

(10) Patent No.: US 11,028,431 B2
(45) Date of Patent: Jun. 8, 2021

(54) DETECTION OF SHORT HOMOPOLYMERIC REPEATS

(71) Applicant: Biocartis NV, Mechelen (BE)

(72) Inventors: Bart Claes, Mechelen (BE); Rudi Rossau, Mechelen (BE)

(73) Assignee: BIOCARTIS, NV, Mechelen (BE)

( * ) Notice: Subject to any disclaimer, the term of this patent is extended or adjusted under 35 U.S.C. 154(b) by 0 days.

(21) Appl. No.: 15/756,806

(22) PCT Filed: Sep. 22, 2016

(86) PCT No.: PCT/EP2016/072605
§ 371 (c)(1),
(2) Date: Mar. 1, 2018

(87) PCT Pub. No.: WO2017/050934
PCT Pub. Date: Mar. 30, 2017

(65) Prior Publication Data
US 2018/0371537 A1    Dec. 27, 2018

(30) Foreign Application Priority Data

Sep. 22, 2015 (EP) .................... 15186341

(51) Int. Cl.
*C12Q 1/68* (2018.01)
*C12Q 1/6858* (2018.01)
*C12Q 1/6886* (2018.01)
*C12N 15/11* (2006.01)

(52) U.S. Cl.
CPC ............ *C12Q 1/6858* (2013.01); *C12N 15/11* (2013.01); *C12Q 1/6886* (2013.01); *C12N 2310/313* (2013.01); *C12N 2310/3517* (2013.01); *C12Q 2527/107* (2013.01); *C12Q 2537/143* (2013.01); *C12Q 2565/1025* (2013.01); *C12Q 2600/158* (2013.01)

(58) Field of Classification Search
None
See application file for complete search history.

(56) References Cited

U.S. PATENT DOCUMENTS

| | | | |
|---|---|---|---|
| 6,664,064 B1 | 12/2003 | Dietmaier | |
| 2005/0053942 A1* | 3/2005 | Kauppinen | C12N 15/1006 435/6.12 |
| 2014/0329245 A1* | 11/2014 | Spier | C12Q 1/686 435/6.12 |
| 2015/0197786 A1* | 7/2015 | Osborne | C12Q 1/6806 435/6.11 |

FOREIGN PATENT DOCUMENTS

| | | |
|---|---|---|
| EP | 1748083 A1 | 1/2007 |
| WO | 2013153130 A1 | 10/2013 |

OTHER PUBLICATIONS

Ahern, The Scientist 9 (15): 20 (1995).*
New England BioLabs 2013-2014 Catalog (2013) (p. 86).*
Claes, "A novel fully integrated molecular diagnostics platform with broad sample prep capabilities", Apr. 2013 (https://media.biocartis.com/biocartis/documents/biocartis_poster_sample_prep_2013_Claes_et_al.pdf).
International Search Report for PCT/EP2016/072605 dated Feb. 6, 2017.
Written Opinion for PCT/EP2016/072605 dated Feb. 6, 2017.
Buhard, Olivier, et al., Multipopulation Analysis of Polymorphisms in Five Mononucleotide Repeats Using to Determine the Microsatellite Instability Status of human Tumors, J of Clinical Oncology, Jan. 10, 2006, pp. 241-251, vol. 24, No. 2.
Pyatt, Robert, et al., Short Communication Polymorphic Variation at the BAT-25 and BAT-26 Loci in Individuals of African Origin, Implications for Microsatellite Instability Testing, Am. J of Pathology, Aug. 1999, vol. 155, No. 2.

* cited by examiner

*Primary Examiner* — James Martinell
(74) *Attorney, Agent, or Firm* — Quarles & Brady LLP

(57) ABSTRACT

The present application relates to detection of changes in the number of nucleotides in short homopolymeric nucleic acid repeats, in particular in short homopolymeric microsatellites, for example for the purpose of diagnosing microsatellite instability (MSI) and/or mismatch repair (MMR-) deficiency in tumors. Accordingly, methods are provided for detecting changes in the number of nucleotides present in short homopolymeric nucleotide repeat sequences as well as kits and cartridges for automated detection of said changes.

13 Claims, 4 Drawing Sheets

Specification includes a Sequence Listing.

DETECTION OF SHORT HOMOPOLYMERIC REPEATS

CROSS-REFERENCE TO RELATED PATENT APPLICATIONS

The present application is a U.S. National Phase application of International Application No. PCT/EP2016/072605, filed on Sep. 22, 2016, which application claims the benefit of priority to European Patent Application No. 15186341.0, filed on Sep. 22, 2015, the contents of which are incorporated herein by reference in their entireties.

TECHNICAL FIELD

The present application relates to detection of changes in the number of nucleotides in short homopolymeric nucleic acid repeats, in particular in short homopolymeric microsatellites, for example, for the purpose of diagnosing microsatellite instability (MSI) and/or mismatch repair (MMR-) deficiency in tumors. Accordingly, methods are provided for detecting changes in the number of nucleotides present in short homopolymeric nucleotide repeat sequences as well as kits and cartridges for automated detection of said changes.

BACKGROUND OF THE INVENTION

DNA mismatch repair (MMR) is an evolutionarily conserved system of multiple factors for recognizing and repairing faulty insertions or deletions ("indels") of bases into the genome, which can arise during replication or recombination, or during repair of some forms of DNA damage. In line with the above, there exists evidence that impaired MMR correlates with genomic instability and thus also is implicated in cancer progression.

Indeed, MMR-deficiency has been described in several cancer types including leukemia, ovarian, pancreatic, or gastric cancer, and is an established cause Lynch cancer-susceptibility syndrome that is responsible for 2-5% of all endometrial (EM) or colorectal (CRC) tumors (Jiricny, 2006). Importantly, MMR-deficient tumors show different prognosis and therapeutic outcome following standard cancer treatments (Ng and Schrag, 2010). For example, MMR-deficient tumors from CRC patients do not seem to respond to 5-fluorouracil-based chemotherapy (Fischer et al., 2007), which is the first-choice chemotherapy for CRC. Furthermore, MMR-deficient tumors also tend to be resistant to cisplatin and carboplatin, which are frequently used in EM cancer treatment (Newish et al., 2010). Finally, these tumors were also observed to relatively quickly develop resistance to targeted therapies, possibly due to their increased mutability and thus also easier acquisition of secondary mutations that potentially can affect other anti-cancer defenses.

Due to the fact that MMR-deficiency was shown to affect patients' response to cancer treatments, its effective detection may potentially have profound consequences on effective management of patients and on their survival. Due to the complexity of the mutations that affect MMR pathway, in clinical practice it is more common to test MMR-deficiency by screening for its direct consequence being errors in DNA replication, rather than performing detailed screening for selected mutations in MMR genes such as MLH1, MSH2, MSH6, or PMS2 (Peltomaki, 1997). These errors in DNA replication are best manifested in changes in length variation at short tandem repeat sequences called microsatellites, a phenomenon referred to as microsatellite instability or MSI.

The microsatellites are tracts of typically 5-to-50 times repeated adjacent (i.e. repeated in tandem) DNA motifs of one to five nucleotides. They are widely distributed throughout the entire mammalian genome and are most frequently located in its non-coding parts. For this reason, many microsatellites are biologically silent, which allows them to accumulate harmless mutations over generations, which can be used for DNA fingerprinting or other identification purposes. However, clonal loss (deletion) or gain (insertion) of one or more microsatellite repeat units in multiple microsatellites in a single individual's tissue but not in the surrounding tissue, is a hallmark of defective replication and strongly suggests impaired MMR and propensity of developing cancer (Pinol et al., 2005).

Currently, the golden standard of MSI analysis involves a PCR-based testing in cancer patients' DNA for the length of at least 5 microsatellite markers including 2 mono- or homopolymers (BAT25, BAT26) of 25 and 26 nucleotides in length, and of 3 dinucleotide repeats (D2S123, D5S346, D17S250) (Boland et al, 1998). The panel of these 5 MSI markers was first proposed by the National Cancer Institute Research Workshop in Bethesda, Md., and therefore is now broadly known as the Bethesda panel. A sample tested with the Bethesda panel is designated as having a high-frequency of MSI or an "MSI-H" phenotype if 30% or more of the markers (so at least 2 in the 5 marker panel) were tested as unstable. If one marker out of five (or <30% of tumor markers) scores as MSI positive, a sample is designated as MSI-low or "MSI-L". Finally, if no marker is found altered, a sample is considered MSI-stable or "MSS" (Boland et al, 1998).

Despite being the current MSI testing standard, the Bethesda panel tends to show low sensitivity, especially for cancers other than colorectal cancer in view of which it was initially developed (Boland et al, 1998). Therefore, alternative markers have widely been tested including the ones mentioned in e.g. Murphy et al, 2006 and Garcia-Alfonso 2012, and WO2013153130.

Another drawback of the currently known approaches is their level of complication, need of specialized instruments extending beyond the standard laboratory thermocyclers, as well as their limited feasibility for automation. The currently existing detection techniques for MSI apply one of these principles: (i) use of fluorescently labelled primers for detection of the Bethesda panel markers, followed by capillary electrophoresis; (ii) high-resolution melting curve analysis of the 5 Bethesda panel markers using a dsDNA-intercalating dye; (iii) mass spectrometric detection of alleles of a different length; and (iv) next-generation sequencing of large DNA regions (e.g. exome), followed by counting the number of mutations.

For example, (i) the initial PCR-based Bethesda screening strategy requires an expert observer's interpretation which hinders effective and straightforward automation. Then, (ii) the high-resolution melting curve analysis with dsDNA-intercalating dyes also using the long Bethesda panel markers, although in principle adaptable to standard PCR thermocyclers, suffers from very limited multiplexing abilities for screening several different MSI markers in one run since the melting temperature for each marker amplicon needs to be sufficiently different as not to produce overlapping signals. Furthermore, as this strategy relies on formation of heteroduplexes between normal and mutant length alleles, it also less sensitive as compared to the other alternatives. Next, (iii) the mass spectrometry-based method (Zhao et al, 2014) is in principle also amenable to automation but requires specialized instrumentation and highly skilled personnel for the data interpretation. Lastly, (iv) MSI status detection by next-generation sequencing (NGS) and counting the number of observed mutations undoubtedly has the advantage of looking at a very large number of positions in the genome or exome rather than only at the selective markers with high sensitivity for MSI. However, although this method is also in principle at least partially automatable, it is currently very expensive, requires a specialized NGS instrument, and remains time-consuming and complicated due to generation of a large amount of data that still needs to be analyzed by a specialist.

Thus, the currently existing techniques for determining MSI status all have certain drawbacks, either related to their limited detection capabilities, costs and turnaround time, or requirement of specialized additional equipment and highly-trained expert's interpretation of the results. The present invention solves the above-listed problems by providing a highly sensitive, multiplexing-suitable, and entirely automatable method for detection of nucleotide number changes in short homopolymeric microsatellites that can be used by any standard quantitative PCR thermocycling instrument. This and other advantages of the present invention are presented in continuation.

SUMMARY OF THE INVENTION

The present invention is defined in the appended independent claims. Preferred embodiments are defined in the dependent claims. In particular, the present invention concerns a method for detecting changes in the number of nucleotides present in a homopolymeric nucleotide repeat sequence equal to or shorter than 15 bp in length, the method comprising the steps of:

generating amplicons by amplifying a nucleic acid sequence comprising the target homopolymeric repeat sequence;

heating the generated amplicons in the presence of at least one signal-generating oligonucleotide probe comprising a sequence capable of hybridizing to the target homopolymeric repeat sequence, and detecting the changes in the strength of the signal generated by said probe in the function of temperature to obtain at least one melting curve; and deducing the number of nucleotides present in the target homopolymeric repeat sequence from the at least one melting curve;

In a preferred embodiment, the method of the present invention uses fluorescently-labeled probes to detect length variations in the short homopolymeric repeat regions in a standard quantitative PCR thermocycling instrument without the need for any additional equipment for post-PCR analysis. Thus, in a particularly advantageous embodiment, the signal-generating reagent is at least one labeled (i.e. signal-generating) oligonucleotide probe, preferably being a molecular beacon probe, comprising a sequence complementary to the target homopolymeric repeat sequence and capable of hybridizing to said target homopolymeric repeat sequence and its specific flanking sequence. Most preferably, the sequence capable of hybridizing to the target homopolymeric repeat sequence comprises a sequence identical to or perfectly complementary to a mutant of said target homopolymeric repeat sequence, said mutant comprising a deletion of at least one homonucleotide in said target homopolymeric repeat sequence as compared to its wild-type form.

In a further aspect, the present invention provides a kit, preferably in a form of a cartridge, for detecting changes in the number of nucleotides present in a target homopolymeric nucleotide repeat sequence equal to or shorter than 15 bp in length, said kit comprising at least one, preferably a plurality of oligonucleotide probes being molecular beacons, each comprising a sequence capable of hybridizing to a sequence comprising a different target homopolymeric repeat sequence equal to or shorter than 15 bp in length; said kit preferably also comprising a proofreading polymerase. Advantageously, each of said molecular beacon probes comprises a sequence capable of hybridizing to different target homopolymeric nucleotide repeat sequences and being identical to or complementary to at least single homonucleotide deletion mutant sequences of each of said different target homopolymeric repeat sequences.

Finally, the present invention also provides uses of provided herein methods, kits, and/or cartridges for the detection of microsatellite instability (MSI), in particular in a sample from a cancer patient.

BRIEF DESCRIPTION OF FIGURES

For a fuller understanding of the nature of the present invention, reference is made to the following detailed description taken in conjunction with the accompanying drawings in which.

DETAILED DESCRIPTION OF THE INVENTION

The present invention concerns new methods, kits, and cartridges, as well as uses thereof, for detecting even very small changes in the number of nucleotides (e.g. +/−1 nt) present in a short, i.e. at least 10 nucleotides shorter than Bethesda the panel marker BAT25 homopolymeric nucleotide repeat sequences. In line with this, the present invention provides the methods, kits, and cartridges, as well as uses thereof, for the detection of instability of short (<15 bp, preferably <12 bp) homopolymeric microsatellite markers, for example such as the ones described in WO2013153130.

In particular, the present invention concerns a method for detecting changes in the number of nucleotides present in a homopolymeric nucleotide repeat sequence equal to or shorter than 15 bp, preferably 12 bp in length, the method comprising the steps of:

generating amplicons by amplifying a nucleic acid sequence comprising the target homopolymeric repeat sequence;

heating the generated amplicons in the presence of at least one signal-generating oligonucleotide probe comprising a sequence capable of hybridizing to the target homopolymeric repeat sequence, and detecting the changes in the strength of the signal generated by said probe in the function of temperature to obtain at least one melting curve; and deducing the number of nucleotides present in the target homopolymeric repeat sequence from the at least one melting curve.

The provided herein method has the advantage of being fully automatable and adaptable to any standard quantitative PCR thermocycling instrument, which allows it to be performed by regular laboratory personnel without the need of specialized training. In addition to the above, the method is highly sensitive, multiplexing-suitable, can provide an estimate of the relative amounts of the detected homopolymeric nucleotide repeat sequences and the variants thereof.

The currently existing methods for MSI detection suffer from the following disadvantages:
(a) to determine repeat length they either require additional specialized equipment for performing post-PCR analysis and/or this analysis typically needs to be interpreted by a highly trained expert; or
(b) in case of high-resolution melting curve with dsDNA-intercalating dyes, the disadvantage is very limited multiplexing capacity in order to avoid overlapping melting signals from different amplicons, and further, it provides no ability to quantify the relative amounts of instable (mutant) sequences to the stable (wild-type) ones.

The present application overcomes these drawbacks by preforming the melting curve-analysis using highly sensitive to mutants fluorescently-labeled probes, in which each marker can be detected in a different fluorescent channel. In a particularly preferred for its sensitivity embodiment, the sequence in the probe capable of hybridizing to the target homopolymeric repeat sequence comprises a sequence identical to or complementary to a mutant sequence the target homopolymeric repeat sequence, said mutant comprising a deletion of at least one homonucleotide in said target homopolymeric repeat sequence as compared to the wild-type (i.e. the expected) form.

Along these lines, in an preferred embodiment, a method is provided for detecting changes in the number of nucleotides present in a homopolymeric nucleotide repeat sequence equal to or shorter than 15 bp in length, the method comprising the steps of:

generating amplicons by amplifying a nucleic acid sequence comprising the target homopolymeric repeat sequence and its specific flanking sequences;

detection of a signal generated by a probe specifically hybridising to the homopolymeric repeat sequence and its flanking sequences; and deducing the number of nucleotides present in the target homopolymeric repeat sequence;

said method being characterised in that the probe comprises a sequence identical to or complementary to a mutant sequence of said target homopolymeric repeat sequence, wherein said mutant sequence comprises a deletion of at least one homonucleotide in said target homopolymeric repeat sequence as compared to the expected wild-type form of the target homopolymeric repeat sequence.

As used herein, the term "nucleic acid" and its equivalent "polynucleotide", as used herein, refer to a polymer of ribonucleosides or deoxyribonucleosides comprising phosphodiester linkages between nucleotide subunits. Nucleic acids include but are not limited to DNA and RNA, e.g. including genomic DNA, mitochondrial or meDNA, cDNA, mRNA, rRNA, tRNA, hnRNA, microRNA, lncRNA, and various modified versions thereof. Nucleic acids can most commonly be obtained from natural sources like biological samples obtained from different types of organisms. On the other hand, nucleic acids can also be synthesized, recombined, or otherwise produced in any of the known human-devised methods (e.g. PCR).

Naturally, in a preferred embodiment, the amplifying is preferably performed by polymerase chain reaction or PCR using a means for performing PCR such as a thermocycler. Advantageously, for better automation purposes, the PCR is preferably performed using means for performing qPCR which provides for easy monitoring of signals generated from the signal generating reagent.

The term "quantitative PCR" or simply "qPCR" is herein given the definition of a laboratory technique based on the polymerase chain reaction (PCR), which is used to amplify and simultaneously detect or quantify a targeted DNA molecule. In contrast to standard PCR where the product of the reaction is detected at its end, i.e. after thermocycling has finished, the key feature of qPCR is that the DNA product is being detected during thermocycling as the reaction progresses in "real time"; hence, the alternative name of qPCR "real-time PCR". There currently exist many different types of qPCRs. For example, when starting with a reverse transcription (RT) step, qPCR can be used to quantify numbers of messenger RNAs and is then called a reverse transcriptase qPCR or an RT-qPCR. As used herein the terms "quantitative PCR" or simply "qPCR" will be employed with preference over the term "real-time PCR" or "RT-PCR" in order to avoid confusion with reverse transcription PCR, also frequently abbreviated as RT-PCR. Most qPCRs use one of the two most common methods for detecting the product amplification in real-time: (a) intercalation of non-specific fluorescent dyes with any double-stranded DNA, or (2) sequence-specific DNA probes consisting of oligonucleotides that are labelled with a fluorescent reporter which permits detection only after hybridization of the probe with its complementary target sequence. The fluorescent signals generated during thermocycling are detected by an appropriate optical detection system and tracked from the moment they pass the background threshold till the reaction reaches plateau. The copy number of the target sequences can be estimated using either relative or absolute quantification strategy, typically by analyzing the shape of the obtained amplification curve (standard curve strategy) or by determining when the signal rises above some threshold value (often called the Ct value, but soe times also Cp value or Cq value). In relative quantification, the target nucleic acid levels estimated in a given sample using the Ct or standard curve analysis are expressed as relative to values obtained for the same target in another reference sample, for example, an untreated control sample. Conversely, in absolute quantification the qPCR signal is related to input copy number using a standard curve or can also be calculated according to a more recent digital PCR method. For the moment being, the first strategy is still more prevalent and bases the estimation of the target DNA amount by comparing the obtained values with a previously made standard curve. These and other qPCR quantification strategies are broadly known in the art and their calculation can differ in smaller or greater depending on a given application and a qPCR system.

As used herein, the term "means for performing quantitative PCR" shall be understood as minimum necessary arrangement of reagents and elements for performing a qPCR. They will usually include any reagents allowing detectable in real time PCR thermocycling of a nucleic acid template received from a source of nucleic acid. Such reagents include but depending on the type of qPCR are not limited to a PCR-grade polymerase, at least one primer set a detectable dye or a probe, dNTPs, PCR buffer etc. Further, the "means for performing quantitative PCR" will usually also include any standard known in the art minimal assembly of parts, which usually includes but is not limited to the following: (1) a suitable compartment (further referred to as a "a thermocycling qPCR compartment") where the real time-detectable thermocycling can take place. Such compartments can e.g. be formed by a chamber suitable for amplifying nucleic acids, i.e. made from appropriate material and providing for sufficient internal temperature regulation, and also comprising at least one wall allowing real-time detection of signals generated during such amplification, e.g. a wall transparent to light. Further, (2) means for varying temperature in this chamber or other compartment, as broadly known from various existing thermocycling machines. Then, (3) means for detecting the signals generated during the qPCR thermocycling, like an optical detector coupled to a computer etc. In brief, such minimal assembly will normally include any known in the art system or systems capable of initiating and maintaining the thermocycling reaction in the thermocycling qPCR compartment, adjusting and regulating the temperature to ensure stable thermocycling conditions therein etc.; further, it will also include any appropriate detection device or devices, means for data processing (e.g. a computer alternatively connected to a database), and output systems allowing to read and monitor the thermocycling of the qPCR reaction in real-time (usu. a computer screen displaying the reaction progress in an appropriate graphic user interface); as well as any software packages suitable for operating the machinery and/or displaying and possibly also aiding the interpretation of the obtained results.

In principle, in possible embodiments, any target-specific oligonucleotide probe suitable for performing melting curve analysis can be used in the method of the invention. Preferred known probes may comprise a pair consisting of a fluorophore and a quencher, and may also advantageously form secondary structures such as loops or hairpins.

In a preferred embodiment, the at least one labeled oligonucleotide probe is a molecular beacon oligonucleotide probe. The molecular beacon probes, or molecular beacons, are hairpin shaped molecules with an internally quenched fluorophore whose fluorescence is restored when they bind to a target nucleic acid sequence. For this reason, molecular beacons are not degraded by the action of polymerase and can be employed in studying their hybridization kinetics to their target via melting curve calling. A typical molecular beacon probe is about 25 nucleotides long but can be longer. Usually, at least the middle 15 nucleotides are complementary to its nucleic acid target while the five nucleotides at each terminus are complementary to each other, which allows the beacon to assemble into a loop or hairpin structure. A molecular beacon that is not hybridized to its target can be divided into 4 structural parts: (1) the loop, which is an 18-30 bp region that is complementary to and hybridizes the target sequence; (2) the stem that is formed by terminal 5-7 nucleotides of both ends of the loop complementarily bound to each other; (3) the fluorophore covalently attached at the 5' end of the molecular beacon; and (4) the quencher covalently attached to the molecular beacon's 3' end. Such structure ensures that when the beacon is not hybridized to its target and closed in the hairpin structure, the quencher quenches the fluorescent emission of the dye such that no signal is generated. But when hybridization occurs, a duplex is formed between the nucleic acid target and the loop of the molecular beacon which breaks the hairpin structure, removes the quencher from the dye, and ultimately results in generation of the fluorescent signal.

In a preferred embodiment of the above embodiment, the molecular beacon oligonucleotide probe comprises a sequence identical to or complementary to a homopolymeric repeat sequence mutant comprising a deletion of at least one homonucleotide in the target homopolymeric repeat sequence. Such molecular beacon design allows to specifically detect with high sensitivity selected MSI markers wherein polymerase slippage errors have occurred, while at the same time remaining sufficiently sensitive to wild-type (i.e. expected) marker forms having at least one homonucleotide longer repeats. It should be remarked that with the term "target homopolymeric nucleotide repeat sequence" it is meant the wild-type or reference homopolymeric repeat sequence as it is expected in the conditions where no MSI is present. Conversely, by "mutant homopolymeric nucleotide repeat sequence" it is meant a homopolymeric nucleotide repeat sequence comprising an insertion or a deletion of at least one homonucleotide in the homopolymeric repeat sequence.

Because of the thus conferred specificity of a given molecular beacon probe to one homopolymeric repeat marker and the unstable (mutant) variants thereof, it also possible to design a multiplexing assay, wherein at least two molecular beacon probes are used in one reaction tube or compartment.

Thus, in a particularly advantageous embodiment, a method is provided wherein at least a second molecular beacon oligonucleotide probe differently labeled than the first molecular beacon oligonucleotide probe is used, wherein said second molecular beacon oligonucleotide probe comprises a sequence capable of hybridizing to a second target homopolymeric nucleotide repeat sequence being different from the first target homopolymeric nucleotide repeat sequence.

Preferably particularly specific molecular beacon probes are used. Thus, in an advantageous embodiment a method is provided wherein the second target homopolymeric nucleotide repeat sequence comprises a sequence identical to or complementary to a mutant sequence comprising a deletion of at least one homonucleotide in said second target homopolymeric repeat sequence.

During amplification of homopolymeric repeat regions, polymerase slippage is known to occur. This leads to mistakes in copying the original number of repeated nucleotides, causing the accumulation of artificial deletions or insertions in the amplified PCR product. Therefore, in another preferred embodiment of the method of the invention, the step of generating amplicons is performed in a PCR comprising a proofreading polymerase, i.e. a polymerase having 3'-5' exonuclease activity. Many such PCR-grade polymerases are known and commercially available. Examples include but are not limited to polymerases like Q5, Pfx, Pfu, Ex Taq etc.

In a further development of the above embodiment, in order to protect to the oligonucleotide probes from the potential threat that the 3'-5' exonuclease activity of the proofreading polymerase may pose, it is advantageous to structurally modify the beacons in such ways that they cannot be digested. Thus, in a particularly advantageous embodiment of the method of the invention, especially from the assay stability point of view, the at least one signal-generating labeled oligonucleotide probe comprises a structural feature or modification protecting said probe from the 3'-5' exonuclease activity of the polymerase, said structural feature or modification preferably being selected from:
  inverted dT at the 3' end of the probe;
  at least one phosphorothioate linkage positioned before any of the last three nucleotides at the 3'end of the probe.

It has been observed that depending on the proofreading polymerase, some proofreading polymerases do not digest certain molecular beacons whose stem is made by certain sequences. This unexpected observation likely results from the fact that molecular beacon stems depending on their sequences have different 3D structures. Therefore, it could be hypothesized that certain proofreading polymerases are incapable of attacking molecular beacons whose stem structure is incompatible with the catalytic center of the proofreading polymerase. Irrespective of the mechanism, we have observed that provision of some types of molecular beacon stems can render them completely immune to 3'-5' exonuclease activity of certain proofreading polymerases. In line with the above, in an alternative embodiment, a method is provided wherein the sequence-specific probe is a molecular beacon oligonucleotide probe and wherein the protective structural feature or modification is a 3'-5'exonuclease-activity resistant stem. Such stems can be easily transplanted to a molecular beacon of interest by any cloning or nucleic acid recombination technique known in the art.

One of the major advantages of the method of the invention is its straightforward automation and adaptation, especially onto known standard qPCR systems. Therefore, in a particularly preferred embodiment, a method of the invention is provided wherein the steps of:
  generating amplicons by amplifying a nucleic acid sequence comprising the target homopolymeric repeat sequence;
  heating the generated amplicons in the presence of a signal-generating oligonucleotide probe, and detecting the changes in the strength of said signal in the function of temperature to obtain at least one melting curve; and deducing the number of nucleotides present in the target homopolymeric repeat sequence from the at least one melting curve
are performed in an automated system. A particularly suitable system for such automation is a Biocartis Idylla platform, which further provides for automation of sample processing.

Advantageously, a method in accordance with the above-described embodiment of the invention can be provided, wherein said method is preceded by any of the following steps:
  providing a source of a nucleic acid potentially comprising the target homopolymeric repeat sequence, preferably said source being a biological sample;
  liberating and/or isolating the nucleic acid potentially comprising the target homopolymeric repeat sequence from the source of a nucleic acid;
  providing said liberated and/or purified nucleic acid potentially comprising the target homopolymeric repeat sequence to the step of generating amplicons;
  wherein at least the steps of:
  liberating and/or isolating the nucleic acid potentially comprising the target homopolymeric repeat sequence from the source of a nucleic acid;
  providing said liberated and/or purified nucleic acid potentially comprising the target homopolymeric repeat sequence to the step of generating amplicons;
are also performed in an automated system.

In a further, particularly advantageous and requiring minimal handling and technical preparation embodiment of the above embodiment, a method can be provided wherein at least steps of:
  liberating and/or isolating the nucleic acid potentially comprising the target homopolymeric repeat sequence from the source of a nucleic acid;
  providing said liberated and/or purified nucleic acid potentially comprising the target homopolymeric repeat sequence to the step of generating amplicons;
  generating amplicons by amplifying a nucleic acid sequence comprising the target homopolymeric repeat sequence; and
  heating the generated amplicons in the presence of a signal-generating oligonucleotide probe and detecting the changes in the strength of said signal in the function of temperature to obtain at least one melting curve;
are performed in a cartridge engageable with said automated system.

As used herein, the term "cartridge" is to be understood as a self-contained assembly of chambers and/or channels, which is formed as a single object that can be transferred or moved as one fitting inside or outside of a larger instrument suitable for accepting or connecting to such cartridge. Some parts contained in the cartridge may be firmly connected whereas others may be flexibly connected and movable with respect to other components of the cartridge. Analogously, as used herein the term "fluidic cartridge" shall be understood as a cartridge including at least one chamber or channel suitable for treating, processing, discharging, or analyzing a fluid, preferably a liquid. An example of such cartridge is given in WO2007004103. Advantageously, a fluidic cartridge can be a microfluidic cartridge. In the context of fluidic cartridges the terms "downstream" and "upstream" can be defined as relating to the direction in which fluids flow in such cartridge. Namely, a section of a fluidic path in a cartridge from which a fluid flows towards a second section in the same cartridge is to be interpreted as positioned upstream of the latter. Analogously, the section to which a fluid arrives later is positioned downstream with respect to a section which said fluid passed earlier.

In general, as used herein the terms "fluidic" or sometimes "microfluidic" refers to systems and arrangements dealing with the behavior, control, and manipulation of fluids that are geometrically constrained to a small, typically sub-millimeter-scale in at least one or two dimensions (e.g. width and height or a channel). Such small-volume fluids are moved, mixed, separated or otherwise processed at micro scale requiring small size and low energy consumption. Microfluidic systems include structures such as micro pneumatic systems (pressure sources, liquid pumps, micro valves, etc.) and microfluidic structures for the handling of micro, nano- and picoliter volumes (microfluidic channels, etc.). Exemplary fluidic systems were described in EP1896180, EP1904234, and EP2419705 and can accordingly be applied in certain embodiments of the presented herein invention.

In a particularly desired embodiment in accordance with the above-listed embodiments, to streamline and facilitate the interpretation of the results of the method according to present invention, the analysis on the melting curve is also performed in an automated manner by means of a computer-implemented software. Such software can be instructed to recognize characteristic position of defined melting peaks (or inflection points) characterizing hybridization of a particular probe to a particular target and obtained by plotting the negative first derivative of a melting curve obtained for said probe and target pair. Hence, in another preferred embodiment, a method of the invention is provided wherein the step of deducing the number of nucleotides present in the target homopolymeric repeat sequence from the at least one melting curve is performed by assessing the position or a relative position of at least one peak of the first derivative of said melting curve, and is most preferably performed in an entirely automated manner.

In further aspect, the present invention also provides kits for performing the method according to the invention. In particular, the present invention provides a kit for detecting changes in the number of nucleotides present in a target homopolymeric nucleotide repeat sequence equal to or shorter than 15 bp in length, said kit comprising at least one molecular beacon oligonucleotide probe, preferably a plurality of molecular beacon oligonucleotide probes, each molecular beacon comprising a sequence capable of hybridizing to a sequence comprising a different target homopolymeric repeat sequence equal to or shorter than 15 bp in length, and preferably said kit also comprising a proofreading polymerase. Preferably, each of said plurality of molecular beacon probes comprises a sequence capable of hybridizing to a particular target homopolymeric nucleotide repeat sequence (preferably being different from the homopolymeric nucleotide repeat sequences targeted by other molecular beacons) and being identical to or complementary to a mutated form of said particular target repeat sequence such that said mutated form misses at least single homonucleotide (i.e. is a deletion) in said target homopolymeric repeat sequence as compared to the wild-type form.

In a preferred embodiment, a kit is provided in a form of a cartridge. Thus, advantageously, the present invention provides a kit wherein said at least one, preferably a plurality of molecular beacon oligonucleotide probes, and preferably also a proofreading polymerase, are provided in a cartridge engageable with an automated system. As described above, a suitable example of a cartridge and an automated system engageable therewith is the Biocartis Idylla platform. Further details of this and similarly applicable to the present invention systems can be found in WO2007004103, EP1896180, EP1904234, and EP2419705. As can be appreciated from the cited herein documents, advantageous cartridges not only comprise means for performing PCR but also may be designed to directly accept a source of nucleic acid or a sample, liberate nucleic acids from said nucleic acid source, and provide (e.g. by pumping) the thus liberated nucleic acid for the subsequent PCR-based assay.

As used herein, the term "source of a nucleic acid" is to be understood as any substance whether liquid or solid, comprising or expected to comprise nucleic acid. A source of nucleic acid can e.g. be an artificially created solution comprising a synthetic or recombinant nucleic acid such as among many other a solution containing a ligation product, an electrophoresis marker (so called "ladder"), a primer stock etc. Most commonly however, a source of nucleic acid will be a biological sample obtained from an organism or cells forming or derived thereof, preferably a clinical sample obtained from a patient.

As used herein, the term "biological sample", or simply "sample", is intended to include a variety of biological sources that contain nucleic acid and/or cellular material, irrespective whether it is freshly obtained from an organism (i.e. fresh tissue sample) or preserved by any method known in the art (e.g. an FFPE sample). Examples of biological samples include: cultures of cells such as mammalian cells but also of eukaryotic microorganisms, body fluids, body fluid precipitates, lavage specimen, fine needle aspirates, biopsy samples, tissue samples, cancer cells, other types of cells obtained from a patient, cells from a tissue or in vitro cultured cells from an individual being tested and/or treated for disease or infection, or forensic samples. Non-limiting examples of body fluid samples include whole blood, bone marrow, cerebrospinal fluid (CSF), peritoneal fluid, pleural fluid, lymph fluid, serum, plasma, urine, chyle, stool, ejaculate, sputum, nipple aspirate, saliva, swabs specimen, wash or lavage fluid and/or brush specimens.

Once a biological sample is provided into the systems or during performing the methods of the invention, it will usually be contacted with a composition to provide a lysate in which nucleic acid is released. As used herein, by "contacting" is meant bringing together, exposing, incubating, or mixing of the sample and the composition. "Releasing" refers to liberating, obtaining and/or reversal of cross-linking. For liberating nucleic acid from a sample, protease activity and pH-buffering may be required from the composition. Releasing may require from the composition potential precipitating activity of components other than nucleic acid present in the investigated sample and removal/dissolving of fixative. Releasing may require conditions such as heating or High-Intensity Focused Ultrasound (HIFU). In one embodiment in accordance with the spirit of the invention, a biological sample is introduced into a cartridge compatible with an automated system such as a diagnostic analyzer, wherein the sample processing steps involving contacting with various solutions and releasing of nucleic acids take place.

Further, the term "means for liberating or purifying nucleic acid from the biological sample" is to be understood as any plurality or chemical reagents and/or physical elements as known in the art that are known to be used for liberating nucleic acids from cells or other structures in a biological sample, and, in case of purification, sufficiently separating said nucleic acids from unwanted sample debris into an acceptably pure form (wherein the term "acceptably" depends on the further purpose of such purified nucleic acids), usually in an aqueous solution. Chemical reagents suitable for such purpose include e.g. any known in the art detergents and/or buffers comprising detergents, chaotropic agents, nuclease inhibitors etc. that are used in tissue or cell disrupting and/or liquefying, and thus releasing nucleic acids contained therein into solution. Similarly, physical elements known in the art to be used in various methods of sample processing for the purpose of nucleic acid liberation/purification include e.g. silica solid supports such as resins in spin columns, silica membranes, beads etc.; further mechanical disruptors or machines generating disruptive energy such as sonicators etc.

In line with the above, advantageously, the present invention also provides a cartridge for automated detection of changes in the number of nucleotides present in a homopolymeric nucleotide repeat sequence equal to or shorter than 15 bp in length, the cartridge comprising a sample compartment for receiving a biological sample;
a means for liberating or purifying nucleic acid from the biological sample received in the sample compartment, said means capable of entering in fluid communication with said sample compartment;
a PCR compartment positioned downstream of the sample compartment and of the means for liberating or purifying nucleic acid, and configured to receive at least a portion of the liberated or purified nucleic acid or at least a portion of the nucleic acid library prepared in the library compartment, said thermocycling PCR compartment further being suitable for amplifying nucleic acids and allowing detection of signals generated during or following such amplification the cartridge characterized in that it further comprises at least one, preferably a plurality of molecular beacon oligonucleotide probes as were described above, and a proofreading polymerase, preferably in the PCR compartment.

In a preferred embodiment, the molecular beacon oligonucleotide probes, and/or the proofreading polymerase can be provided in said cartridge in a spotted format, which contributes to increased shelf-life of such cartridge according to the invention.

Lastly, it is also an object of the invention to provide a use of methods, kits, and cartridges according to the invention for the detection of microsatellite instability (MSI), preferably in a sample obtained from a patient diagnosed with or expected of suffering from a cancer.

EXAMPLES

1. Molecular Beacon Melting Curve for MSI Marker in the TMEM65

The ability of a preferred embodiment of the presented herein method to detect even very minor changes of 1nt in length in a homopolymeric nucleotide repeat sequence will be demonstrated herein using human TMEM65 marker, positioned at Chr8:125325217, and containing a homopolymeric repeat of 11 adenines (A). The wild-type (WT) homopolymeric repeat sequence (bolded and underlined) and its specific surrounding sequence of TMEM65 is given below:

TAAATAAAATTCACTAAATAAGATATAATGAGATTAGGAGTATGAATATG

GGGTATTCAGACTTATTCCATTCAGATGAGAAGATGACATCTTTGGAGGG

AAAAAAAAAAACCTTACCAAATAATATAAATTGTATCTCATTAATCTTTC

AAACATCACTTCAACTTCATCATTTATACCATAAACCTTCTTGACAGTTC

To detect the nucleotide changes in the repeat sequence of TMEM65, a molecular beacon detection probe was designed having the sequence of CGCAC*G* AGGG<u>AAAAAAAAAAA</u> CCTTA*C* GTGCG and was labelled with FAM as a fluorescently labelling molecule, whereas dabcyl was used as a quencher (stem region of the molecular beacon probe is indicated in italics, the probe hybridizing region is bolded wherein the repeat sequence identical to mutated TMEM65 marker comprising 10 adenine repeats instead of 11 is bolded and underlined).

For testing the ability of the TMEM65-specific probe to bind and recognize both the WT TMEM65 marker sequence and its two different mutant counterparts either being a deletion or an insertion of one homonucleotide, 3 synthetic targets of TMEM65 were prepared representing the 3 different variants of the TMEM65 homopolymer repeat. The sequences of the three said variants are given below as DNA strands that are complementary to the TMEM65-specific molecular beacon probe (containing poly-A repeat) which hybridizes to said variants strands. The complementary TMEM65 variant strands (containing poly-T repeat) are the following:

TMEM65_T10 (1 bp deletion):
AAATGATGAAGTTGAAGTGATGTTTGAAAGATTAATGAGATACAATTTAT

ATTATTTGGTAAGGTTTTTTTTTTCCCTCCAAAGATGTCATCTTCTCATC

TGAATGGAATAAGTCTGAATAC

TMEM65_T11 (reference):
AAATGATGAAGTTGAAGTGATGTTTGAAAGATTAATGAGATACAATTTAT

ATTATTTGGTAAGGTTTTTTTTTTTCCCTCCAAAGATGTCATCTTCTCAT

CTGAATGGAATAAGTCTGAATAC

TMEM65_T12 (1 bp insertion):
AAATGATGAAGTTGAAGTGATGTTTGAAAGATTAATGAGATACAATTTAT

ATTATTTGGTAAGGTTTTTTTTTTTTCCCTCCAAAGATGTCATCTTCTCA

TCTGAATGGAATAAGTCTGAATAC

The TMEM65-specific molecular beacon probe was added at concentration of to 200 nM to 3 separate PCR tubes, each containing one of the 3 afore-described variants at the concentration of 2500 nM in a standard PCR reaction buffer. The mixture was then denatured in a Bio-Rad CFX96 instrument for 2 min at 95° C. and then cooled down to 45° C. for 15 min to allow sufficient time for the molecular beacon probe to hybridize to its target. Next, a melting curve analysis was performed by heating the mixture to 75° C. in steps of 0.3° C. (5s per cycle) and fluorescence was measured after every 0.3° C. increase.

Figure 1:
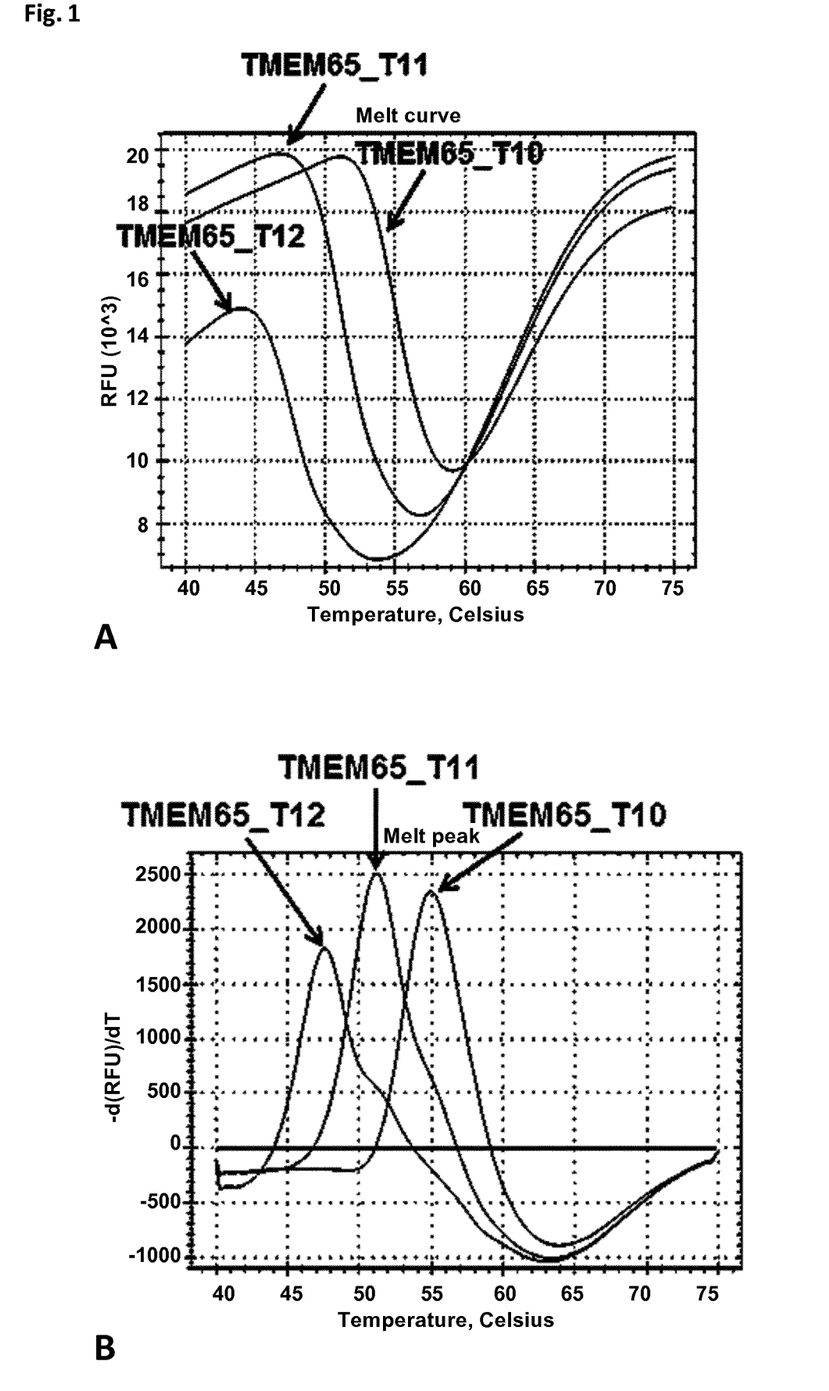
FIG. 1: shows melting curves (panel A) and melting peaks (panel B) characterizing hybridization kinetics in function of temperature for TMEM65-specific molecular beacon probe hybridizing to three target sequences having different number of homonucleotides in the TMEM65 homopolymeric repeat sequence.

The results of the melting curve analysis are shown in FIG. 1, wherein the upper panel A shows melting curves (as fluorescence over time) of the TMEM65-specific probe to the three targets, and wherein the lower panel B shows melting peaks or negative first derivatives of the melting curves in A. The Tm values for the three melting peaks were: 54.9° C. for TMEM65_T10, 51.3° C. for TMEM65_T11, and 47.7° C. for TMEM65_T12. The Delta Tm values of the melting peaks were:

TMEM65_*T*10–TMEM65_*T*11=3.6° C.

TMEM65_*T*11–TMEM65_*T*12=3.6° C.

TMEM65_*T*10–TMEM65_*T*12=7.2° C.

Based on these results it can be concluded that deletion or insertion of a single nucleotide compared to the reference sequence (i.e. the T10 or T12 repeat versus the T11 reference repeat) results in a difference of several ° C. (degrees Celsius) in Tm of the melting peak compared to the Tm of the melting peak for the reference sequence. Therefore, the length of this repeat sequence in the TMEM65 gene can be determined by analysis of the melting peaks produced by hybridization of the described molecular beacon probe onto its target region.

2. Assessment of TMEM65 MSI Marker Status in Cancer Patient Samples

FFPE samples from colorectal cancer patients were provided into Biocartis Idylla fluidic cartridges. The cartridges were closed and loaded onto the Biocartis Idylla platform for automated PCR-based genetic analyses, after which the automated sample processing was initiated. Firstly, the patients' DNA was released from the FFPE samples and then pumped into PCR compartments of the cartridges. Next, asymmetric PCR amplification of the region surrounding the TMEM65 homopolymer repeat sequence was performed in each cartridge using the following primers FWD: 5'-CAGACTTATTCCATTCAGATGAGA-3' and REV:

5'-GAAGTGATGTTTGAAAGATTAATGAGA-3'. The PCR amplification was performed in the presence of the above-described TMEM65-specific molecular beacon probe.

After the PCR, the PCR products were denatured in the cartridges in for 2 min at 95° C. and then cooled down to 45° C. for 15 min to allow sufficient time for the hybridization of the TMEM65-specific molecular beacon probe to its targets. Next, a melting curve analysis was performed while still on Idylla system by heating the mixture from 40° C. to 60° C. in steps of 0.3° C. (5s per cycle) and at the same time monitoring the fluorescence signals after every 0.3° C. increase. Melting peaks were calculated as the negative values of the first derivatives of the obtained melting curves.

Figure 2:
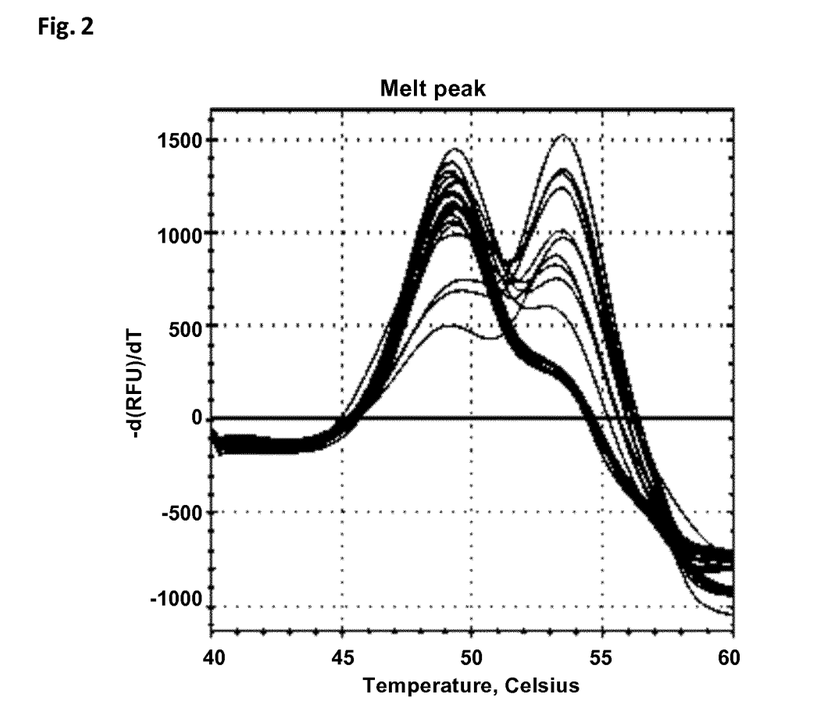
FIG. 2: shows melting peaks characterizing TMEM65 microsatellite stability status in 10 wild-type (WT) and microsatellite stable (MSS) samples (black curves, TMEM65 repeat length 11) and in 10 microsatellite instable (MSI-High [MSI-H]) samples (grey curves, TMEM65 repeat length 10)

FIG. 2 shows the results obtained from 10 wildtype samples (black curves, TMEM65 repeat length 11) considered to be microsatellite stable (MSS) and 10 mutant samples (grey curves, TMEM65 repeat length 10) considered to be microsatellite instable (MSI-High [MSI-H]). Note the consistent peak heights of the wildtype A11 peak (at ±49° C.) in the MSS samples, while in MSI-H samples both the wildtype A11 peak and the mutant A10 peak (at ±53° C.) have variable height. This reflects the variable proportions of wildtype and mutant alleles present in each sample.

Figure 3:
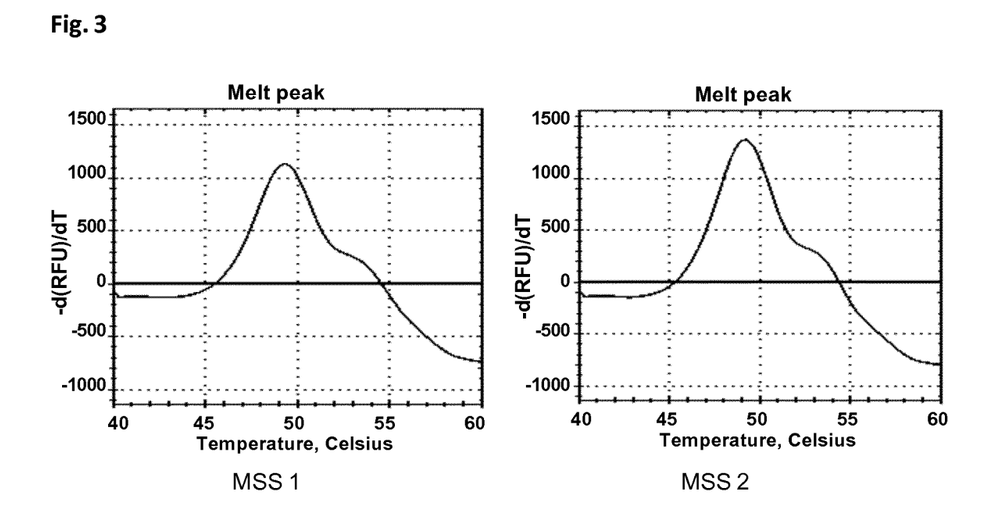
FIG. 3: shows melting peaks of the TMEM65 probe for two randomly selected MSS samples MSS 1 and MSS 2.
Figure 4:
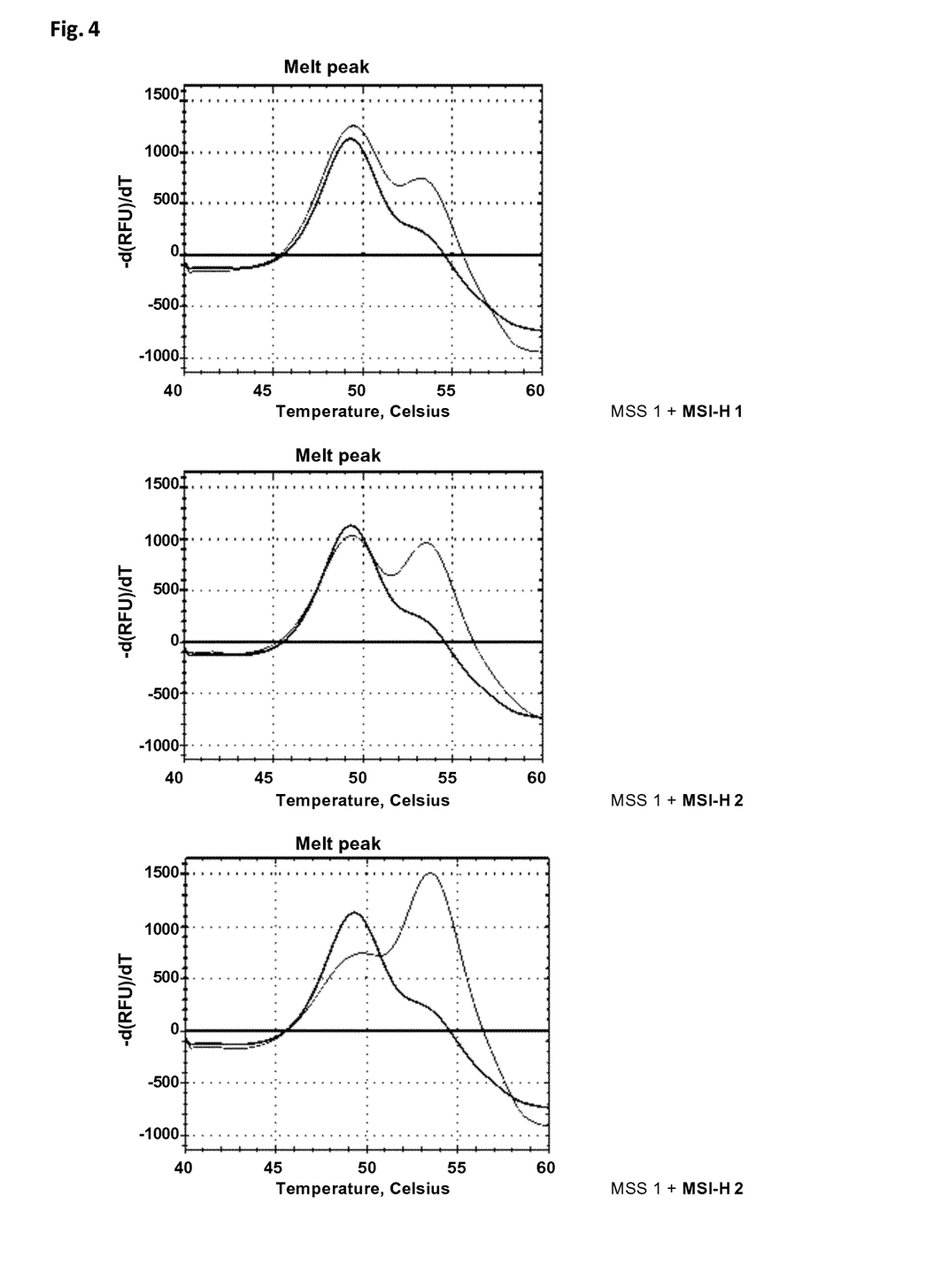
FIG. 4: shows melting peaks of the TMEM65 probe for three randomly selected MSI-H samples (MSI-H 1-3), each shown against a TMEM65 probe melting peak obtained for the MSI-stable sample MSS 1.

FIGS. 3 and 4 show representative examples of MSS and MSI-H FFPE samples, respectively. In FIG. 4, in each of the panels A-C depicting three different MSI-H samples, MSS 1 is shown as a wildtype reference. Sample MSI-H 1 contains a lower of mutant than wildtype allele, since the mutant A10 peak height (at ±53° C.) is lower than the wildtype A11 peak height (at ±49° C.). Sample MSI-H 2 contains similar amounts of mutant and wildtype allele, since the mutant A10 peak height (at ±53° C.) is similar to the wildtype A11 peak height (at ±49° C.). Sample MSI-H 3 contains a higher amount of mutant than wildtype allele, since the mutant A10 peak height (at ±53° C.) is higher than the wildtype A11 peak height (at ±49° C.).

The presented herein results demonstrate that the procedure of using a molecular beacon probe, as described here, allows the determination of the number of nucleotides present in the TMEM65 homopolymer repeat sequence in DNA from colorectal cancer FFPE tissue biopsies. Additionally, this method allows an estimate of the relative amounts of wildtype and mutant TMEM65 repeat alleles present in the DNA from the tumor biopsy.

3. Performance of Different Molecular Beacon Probes in the Presence of a Proofreading Polymerase For achieving greater sensitivity of the described herein method it is advantageous to use in the PCR amplification mixture a proofreading (i.e. an error-correcting) polymerase having 3'-5' exonuclease activity. However, for many molecular beacons in the mixture it was observed that different tested proofreading polymerases may degrade different beacons, which results in partial or complete loss of signal and therefore also interferes with or prevents reliable data interpretation.

Figure 5:
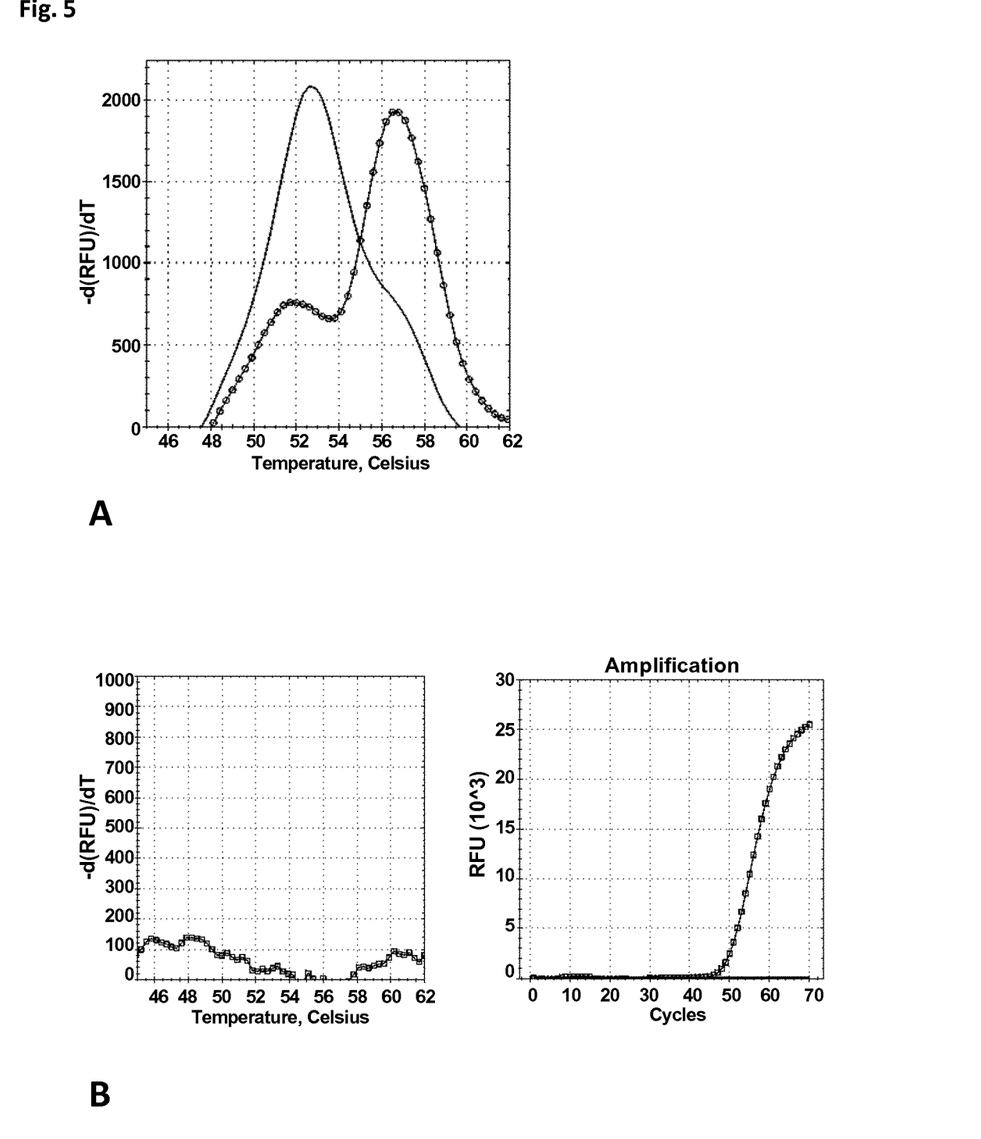
FIG. 5: shows melting peaks for ABAT-marker-specific molecular beacon probes that either comprise (panel A) a stem that is resistant to exonuclease activity of Q5 polymerase, or (panel B) a stem that the Q5 polymerase degrades.

An example of the above is shown in FIG. 5. The upper panel A shows melting peaks obtained on DNA from 2 clinical FFPE samples with a proofreading polymerase Q5 and a molecular beacon probe of a sequence CGCAG-GAAGCTAAAAAAAAAAACCCTTCTGCG (having as a label Texas Red and as a quencher Iowa Black FQ) designed to detect potential homonucleotide losses at an MSI marker ABAT. The continuous darker peak corresponds to an MSS (stable) sample where ABAT is wild type and comprises 11 adenine repeats. The circled line shows a double curve obtained on DNA from an MSI-H sample comprising a higher deletion peak on the right-hand side of the curve and a smaller WT peak on the left-hand side. The WT peak is usually observed in MSI-H tumor samples as there is nearly always tumor tissue contamination with WT DNA from the tumor-surrounding stroma.

Such stable results could repetitively be obtained with other samples when using the Q5 proofreading polymerase and the above-described ABAT-specific molecular beacon without the need of further protecting said beacon with any additional chemical modifications. It has been hypothesized that this likely results from the 3D structure of said beacon's stem which is incompatible to bind to and be digested by the exonuclease active centre of the Q5 polymerase.

A completely different melting profile, shown in the left-hand side of the lower panel B of FIG. 5, was obtained with Q5 polymerase for another molecular beacon specific to ABAT and having the sequence of CCGTCCGAAG-CTAAAAAAAAAAACCCTTGGACGG (same label and quencher). This probe was efficiently and repeatedly degradable by the exonuclease activity of Q5 polymerase during PCR. Since the beacon was being degraded in the course of PCR, no signal could be obtained during post-PCR melting curve analysis (the graph is flat). The right-hand side of panel B shows a qPCR profile for the same probe which demonstrates that the beacon is functional and generates signal during PCR. Since the signal is no longer present in the post PCR melting, this proves that the signal generated during PCR was caused by degradation of the beacon.

It was observed that in PCRs performed using Q5 polymerase but with other molecular beacon probes specific to different MSI makers, the same trend was observed depending on which one of the stems as above-described for the two ABAT-specific probes was present in the given beacon.

The invention claimed is:

1. A method for deducing the number of nucleotides present in a target homopolymeric repeat sequence equal to or shorter than 15bp in length, the method comprising the steps of:
   a) generating amplicons by amplifying a nucleic acid sequence comprising the target homopolymeric repeat sequence;
   b) heating the generated amplicons in the presence of at least one signal-generating oligonucleotide probe comprising a sequence capable of hybridizing to the target homopolymeric repeat sequence, and detecting the changes in the strength of the signal generated by said probe in the function of temperature to obtain at least one melting curve; and
   c) deducing the number of nucleotides present in the target homopolymeric repeat sequence from the at least one melting curve;
   wherein the sequence capable of hybridizing to the target homopolymeric repeat sequence comprises a sequence identical to or complementary to a mutant sequence comprising a deletion of at least one homonucleotide in said target homopolymeric repeat sequence, and
   wherein the step of generating amplicons is performed in a PCR comprising a polymerase having 3'-5' exonuclease activity.

2. The method according to claim 1, wherein the oligonucleotide probe is a molecular beacon oligonucleotide probe.

3. The method according to claim 2, wherein at least a second molecular beacon oligonucleotide probe differently labeled than the first molecular beacon oligonucleotide probe is used, wherein said second molecular beacon oligonucleotide probe comprises a sequence capable of hybridizing to a second target homopolymeric nucleotide repeat sequence being different from the first target homopolymeric nucleotide repeat sequence.

4. The method according to claim 3, wherein the sequence capable of hybridizing to the second target homopolymeric nucleotide repeat sequence comprises a sequence identical to or complementary to a mutant sequence comprising a deletion of at least one homonucleotide in said second target homopolymeric repeat sequence.

5. The method according to claim 1, wherein the at least one signal-generating labeled oligonucleotide probe comprises a structural feature or modification protecting said probe from the 3'-5' exonuclease activity of the polymerase.

6. The method according to claim 5, wherein the sequence- specific probe is a molecular beacon oligonucleotide probe and wherein said structural feature or modification is a 3'-5'exonuclease-activity resistant stem.

7. The method according to claim 5, wherein the structural feature or modification is selected from:
   i) inverted dT at the 3' end of the probe;
   ii) at least one phosphorothioate linkage positioned before any of the last three nucleotides at the 3' end of the probe.

8. The method according to claim 1, wherein the steps a), b), and c) are performed in an automated system.

9. The method according to claim 8, said method preceded by any of the following steps:
   providing a source of a nucleic acid potentially comprising the target homopolymeric repeat sequence;
   liberating and/or isolating the nucleic acid potentially comprising the target homopolymeric repeat sequence from the source of a nucleic acid; and
   providing said liberated and/or purified nucleic acid potentially comprising the target homopolymeric repeat sequence to the step of generating amplicons; and
   wherein at least the steps of:
   liberating and/or isolating the nucleic acid potentially comprising the target homopolymeric repeat sequence from the source of a nucleic acid;
   providing said liberated and/or purified nucleic acid potentially comprising the target homopolymeric repeat sequence to the step of generating amplicons;
   are also performed in an automated system.

10. The method according to claim 9, wherein at least the steps of:
   liberating and/or isolating the nucleic acid potentially comprising the target homopolymeric repeat sequence from the source of a nucleic acid;

providing said liberated and/or purified nucleic acid potentially comprising the target homopolymeric repeat sequence to the step of generating amplicons;

generating amplicons by amplifying a nucleic acid sequence comprising the target homopolymeric repeat sequence; and heating the generated amplicons in the presence of a signal-generating oligonucleotide probe and detecting the changes in the strength of said signal in the function of temperature to obtain at least one melting curve;

are performed in a cartridge engageable with said automated system.

11. The method according to claim 9, wherein the source of a nucleic acid is a biological sample.

12. A method according to claim 1, wherein the deducing the number of nucleotides present in the target homopolymeric repeat sequence from the at least one melting curve is performed by assessing the position or a relative position of at least one peak of the first derivative of said melting curve.

13. The method according to claim 12, wherein said method is performed in an automated manner.

* * * * *

SEQUENCE LISTING

<160> NUMBER OF SEQ ID NOS: 9

<210> SEQ ID NO 1
<211> LENGTH: 200
<212> TYPE: DNA
<213> ORGANISM: Homo sapiens

<400> SEQUENCE: 1

```
taaataaaat tcactaaata agatataatg agattaggag tatgaatatg gggtattcag      60
acttattcca ttcagatgag aagatgacat ctttggaggg aaaaaaaaaa accttaccaa     120
ataatataaa ttgtatctca ttaatctttc aaacatcact tcaacttcat catttatacc     180
```
ataaaccttc ttgacagttc                                              200

<210> SEQ ID NO 2
<211> LENGTH: 31
<212> TYPE: DNA
<213> ORGANISM: Artificial
<220> FEATURE:
<223> OTHER INFORMATION: NA - oligonucleotide probe

<400> SEQUENCE: 2
cgcacgaggg aaaaaaaaaa ccttacgtgc g                                  31

<210> SEQ ID NO 3
<211> LENGTH: 122
<212> TYPE: DNA
<213> ORGANISM: Homo sapiens

<400> SEQUENCE: 3
aaatgatgaa gttgaagtga tgtttgaaag attaatgaga tacaatttat attatttggt   60 aaggttttt ttttccctcc aaagatgtca tcttctcatc tgaatggaat aagtctgaat   120
ac                                                                 122

<210> SEQ ID NO 4
<211> LENGTH: 123
<212> TYPE: DNA
<213> ORGANISM: Homo sapiens

<400> SEQUENCE: 4
aaatgatgaa gttgaagtga tgtttgaaag attaatgaga tacaatttat attatttggt   60 aaggttttt tttttccctc caaagatgtc atcttctcat ctgaatggaa taagtctgaa   120
tac                                                                123

<210> SEQ ID NO 5
<211> LENGTH: 124
<212> TYPE: DNA
<213> ORGANISM: Homo sapiens

<400> SEQUENCE: 5
aaatgatgaa gttgaagtga tgtttgaaag attaatgaga tacaatttat attatttggt   60 aaggttttt tttttcccct ccaaagatgt catcttctca tctgaatgga ataagtctga   120
atac                                                               124

<210> SEQ ID NO 6
<211> LENGTH: 24
<212> TYPE: DNA
<213> ORGANISM: Artificial
<220> FEATURE:
<223> OTHER INFORMATION: NA - primer

<400> SEQUENCE: 6
cagacttatt ccattcagat gaga                                          24

<210> SEQ ID NO 7
<211> LENGTH: 27
<212> TYPE: DNA
<213> ORGANISM: Artificial
<220> FEATURE:
<223> OTHER INFORMATION: NA - primer

<400> SEQUENCE: 7

-continued

```
gaagtgatgt ttgaaagatt aatgaga                                     27

<210> SEQ ID NO 8
<211> LENGTH: 31
<212> TYPE: DNA
<213> ORGANISM: Artificial
<220> FEATURE:
<223> OTHER INFORMATION: NA - oligonucleotide probe

<400> SEQUENCE: 8
cgcaggaagc taaaaaaaaa acccttctgc g                                31

<210> SEQ ID NO 9
<211> LENGTH: 33
<212> TYPE: DNA
<213> ORGANISM: Artificial
<220> FEATURE:
<223> OTHER INFORMATION: NA - oligonucleotide probe

<400> SEQUENCE: 9
ccgtccgaag ctaaaaaaaa aaccttgga cgg                               33
```

UNITED STATES PATENT AND TRADEMARK OFFICE
CERTIFICATE OF CORRECTION

| | |
|---|---|
| PATENT NO. | : 11,028,431 B2 |
| APPLICATION NO. | : 15/756806 |
| DATED | : June 8, 2021 |
| INVENTOR(S) | : Bart Claes et al. |

It is certified that error appears in the above-identified patent and that said Letters Patent is hereby corrected as shown below:

In the Specification

Column 1, Line 50, "Newish" should be --Hewish--.

Signed and Sealed this
Twenty-first Day of February, 2023

Katherine Kelly Vidal
*Director of the United States Patent and Trademark Office*